United States Patent
Apak et al.

(10) Patent No.: US 8,912,004 B2
(45) Date of Patent: Dec. 16, 2014

(54) OPTICAL SENSOR-BASED CUPRIC REDUCING ANTIOXIDANT CAPACITY (CUPRAC) ASSAY

(75) Inventors: Mustafa Resat Apak, Istanbul (TR); Kubilay Guclu, Istanbul (TR); Mustafa Ozyurek, Istanbul (TR); Mustafa Bener, Istabul (TR); Enrique Martinez, Clinton Township, MI (US); Denis Callewaert, Metamora, MI (US)

(73) Assignee: Oxford Biomedical Research, Inc., Rochester Hills, MI (US)

( * ) Notice: Subject to any disclaimer, the term of this patent is extended or adjusted under 35 U.S.C. 154(b) by 0 days.

(21) Appl. No.: 13/435,662

(22) Filed: Mar. 30, 2012

(65) Prior Publication Data
US 2012/0276645 A1 Nov. 1, 2012

Related U.S. Application Data

(60) Provisional application No. 61/480,114, filed on Apr. 28, 2011.

(51) Int. Cl.
*G01N 21/75* (2006.01)
*G01N 21/00* (2006.01)
*G01N 31/22* (2006.01)
*G01N 21/78* (2006.01)

(52) U.S. Cl.
CPC ............... *G01N 21/78* (2013.01); *G01N 31/22* (2013.01)
USPC ........... 436/93; 422/82.05; 422/68.1; 422/50; 436/164

(58) Field of Classification Search
CPC ....... G01N 21/75; G01N 31/22; G01N 31/00; G01N 21/78; G01N 21/00
USPC .......... 436/93, 91, 164, 129, 97, 99; 422/82.05, 68.1, 50
See application file for complete search history.

(56) References Cited

U.S. PATENT DOCUMENTS 4,303,409 A * 12/1981 Ogawa et al. ................... 436/93

OTHER PUBLICATIONS

Bener Mustafa, et al., Development of a Low-Cost Optical Sensor for Cupric Reducing Antioxidant Capacity Measurement of Food Extracts, Anal. Chem, Apr. 23, 2010, 82, 4252-4258.*
Mustafa Ozyurek at al, "The Main and Modified CUPRAC Methods of Antioxidant Measurement" Trends in Analytical Chemistry, 2011, vol. 30, No. 4, pp. 652-664.
Garry R. Buettner, "The Pecking Order of Free Radicals and Antioxidants: Lipid Peroxidation, Tocopherol, and Ascorbate, Archives of Biochemistry and Biophysics", 1993, vol. 300, No. 2, Feb. 1, pp. 535-543.
Paul A. Kilmartin et al., "A Cyclic Voltammetry Method Suitable for Characterizing Antioxidant Properties of Wine and Wine Phenolics", J. Agric Food Chem, 2001, 49, pp. 1957-1965.

* cited by examiner

*Primary Examiner* — Christine T Mui
(74) *Attorney, Agent, or Firm* — Greer, Burns & Crain, Ltd.

(57) ABSTRACT

An example embodiment is an apparatus for measuring antioxidant presence comprising a solid media, and a reagent carried by the media, the reagent reactive with at least one antioxidant to cause changes in light that is incident upon the reagent while carried by the solid media.

9 Claims, 2 Drawing Sheets

OPTICAL SENSOR-BASED CUPRIC REDUCING ANTIOXIDANT CAPACITY (CUPRAC) ASSAY

CROSS REFERENCE AND CLAIM FOR PRIORITY

The present application claims priority on U.S. Provisional Application No. 61/480,114 filed on Apr. 28, 2011; which application is incorporated by reference herein.

TECHNICAL FIELD

One embodiment of the present invention relates to antioxidant assays. More specifically, some embodiments of the present invention relate to optical sensors for detecting antioxidant capacity.

BACKGROUND

The accumulation of reactive oxygen species (ROS) in the organism, unless counterbalanced by antioxidants produced naturally by the body or taken in through the diet, can cause oxidative damage to DNA and cellular membranes under "oxidative stress" conditions eventually giving rise to certain human diseases, especially cardiovascular disease and some types of cancer. In this context, the measurement of antioxidant capacity of food and biological samples through development of selective and sensitive new techniques has recently gained importance.

Various spectroscopic techniques have been developed for measuring the total antioxidant capacity/activity of pure antioxidant compounds, biological fluids, food extracts, and their various components. These solution-based assays can be broadly classified as electron transfer (ET)-based assays (e.g., CUPRAC, Folin, ABTS/TEAC, FRAP) and hydrogen atom transfer (HAT)-based assays (e.g., ORAC, TRAP). In some cases, these two mechanisms are not differentiated with distinct boundaries. In fact, most non-enzymatic antioxidant activity (e.g., scavenging of free radicals, inhibition of lipid peroxidation, etc.) is mediated by redox reactions.

HAT-based assays measure the capability of an antioxidant to quench free radicals (generally peroxyl radicals) by H-atom donation. Since both the fluorescent probe and antioxidants react with peroxyl radical (ROO) in HAT-based assays, antioxidant activity can be determined from competition kinetics by recording the fluorescence decay curve of the probe in the absence and presence of antioxidants, and integrating the area under these curves to take the difference. HAT-based assays basically include oxygen radical absorbance capacity (ORAC), and total peroxyl radical-trapping antioxidant parameter (TRAP) assays using R-phycoerythrin as the fluorescent probe.

In most ET-based assays, the antioxidant action is simulated with a suitable redox-potential probe, i.e., the antioxidants react with a fluorescent or colored probe (oxidizing agent) instead of peroxyl radicals. Spectrophotometric ET-based assays measure the capacity of an antioxidant in the reduction of a chromogenic oxidant, which changes color when reduced. The degree of color change (either an increase or decrease of absorbance at a given wavelength) is correlated to the concentration of antioxidants in the sample. ABTS/TEAC (trolox-equivalent antioxidant capacity) and DPPH are decolorization assays, whereas in Folin total phenolics, FRAP (ferric reducing antioxidant power) and CUPRAC (cupric reducing antioxidant capacity) assays, there is an increase in absorbance at a prespecified wavelength as the antioxidant reacts with the chromogenic reagent (i.e., in the latter two methods, the lower oxidation states of iron and copper, namely Fe(II) and Cu(I), respectively, emerging as a result of the redox reaction with antioxidants form charge-transfer complexes with the ligands). These assays generally set a fixed time for the concerned redox reaction, and measure thermodynamic conversion (i.e., reduction of the colored species) during that period.

ET-based antioxidant assays generally suffer from reproducibility problems, and those assays performed in solution strictly necessitate accurate measurement and control of reagent and sample volumes, pH, reaction conditions, etc. for standardization of assay protocols. This can be difficult in the existing art, particularly if attempting low cost, high volume, low operator skill applications.

Linearity of responses over a reasonable concentration range together with the additivity of total antioxidant capacity (TAC) values for constituents of complex mixtures would be very desirable for meaningful comparison of TAC value of different food or biofluid samples found with the aid of a sensor. To date, these objectives have not been achieved in a reproducible, low cost and easy to use manner.

There remains a need for sensors that can be particularly suited to rapid and low-cost screening applications evaluation of foods and/or biofluids with sensitivity and precision as well as can solve the linearity problems of previous electrochemical sensors. Other unresolved needs likewise exist.

SUMMARY OF THE INVENTION

Some embodiments of the present invention provide for an optical sensor including a Cu(II)-Nc reagent, or any conjugated, heteroatom-containing heterocyclic compound which is capable of chelating a metal and that undergoes changes in its spectral absorbance characteristics based on the oxidation state such that the system has a standard potential of approximately 0.6 V and responds to antioxidants similarly to the $Cu^{2+}$/Nc system immobilized onto a membrane or other solid matrix.

Some embodiments of the present invention provide for a device or a kit including the optical sensor, instructions for use, and materials for taking samples of substances.

Other embodiments of the present invention also provide a preferred method of making an optically transparent optical sensor by thinly slicing Nafion membrane, immersing the membrane in a solution including Cu(II) and Nc, agitating the solution, impregnating the membrane with the Cu(II)-Nc reagent, and producing the Optical sensor.

Still other embodiments of the present invention provide for a method of determining total antioxidant capacity of a substance by applying the optical sensor to a substance, oxidizing the Cu(II)-Nc reagent with antioxidants in the substance and forming a Cu(I)-Nc chelate, detecting the absorbance of the Cu(I)-Nc chelate, and determining the total antioxidant capacity of the substance.

Embodiments of the present invention also provide for a method of determining total antioxidant capacity in a biological sample, such as a body fluid, by applying the optical sensor to the biological sample, oxidizing the Cu(II)-Nc reagent with antioxidants in the biological sample and forming a Cu(I)-Nc chelate on the sensor surface, detecting the absorbance of the Cu(I)-Nc chelate, and determining the total antioxidant capacity in the sample.

A further example embodiment of the invention includes an apparatus for measuring antioxidant presence comprising a solid media, and a reagent carried by the media, the reagent reactive with at least one antioxidant to cause changes in light that is incident upon the reagent while carried by the solid media.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION

Figure 1:
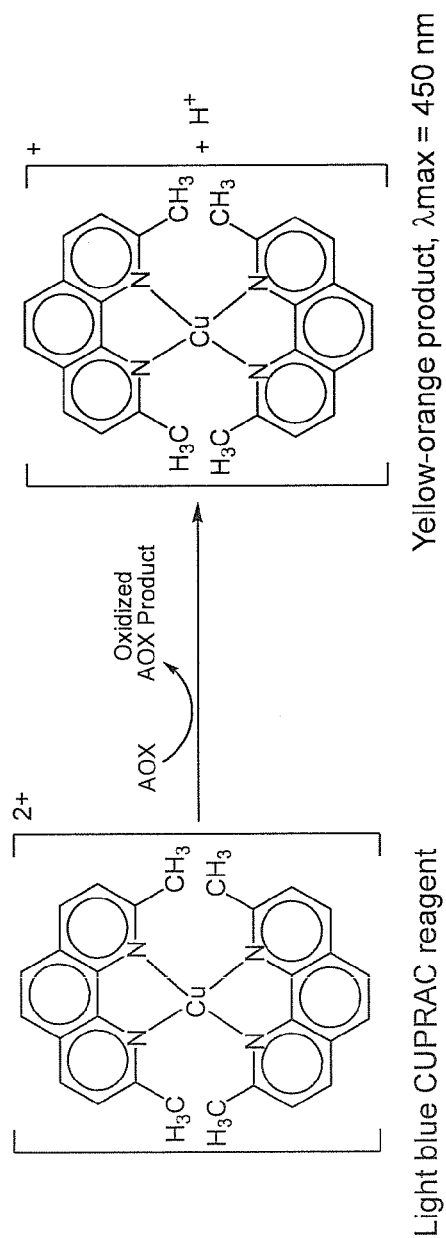
FIG. 1 shows a CUPRAC reaction and a suitable chromophore, neocuproine (Nc)

Some embodiments of the present invention are generally related to the transformation of a solution-based cupric reducing antioxidant capacity (CUPRAC) assay for antioxidants into a polymeric membrane as a solid-state optical test strip (sensor). This sensor is superior over prior art ET-based antioxidant sensors in regards to the linearity of responses versus concentrations, and to the simplicity and versatility of operation. The linear response is present over a wide antioxidant concentration range for standard antioxidant compounds.

The optical sensor includes a copper chelator, complex, selected from neocuproine and other copper chelators with similar properties, immobilized onto a solid media such as a solid phase matrix or the like. Most preferably, for quantification using transmitted light, the optical sensor includes a CUPRAC reagent electrostatically immobilized onto a cation exchanger Nafion membrane. The term "CUPRAC reagent" as used herein is intended to broadly refer to any reagent generally known to be useful in CUPRAC methods, with one example being Cu(II)-Nc reagent. Reagents useful in invention embodiments, including CUPRAC reagents, can also be any other suitable cuproine complex or any conjugated, heteroatom-containing heterocyclic compound which is capable of chelating a metal ion and that undergoes changes in its spectral absorbance characteristics based on the oxidation state such that the system has a standard potential of approximately 0.6 V and responds to antioxidants similarly to the $Cu^{2+}$/Nc system. Other solid media are possible. As an example, the solid phase matrix can also be filter paper or woven fabrics, in which case the change in light reflected from the surface may be compared to a color chart or measured using suitable instrumentation. Preferably, the optical sensor is in the shape of a test strip that can be inserted in or contacted with a substance in order to test for antioxidant capacity. The optical sensor can be made in any suitable size, and preferably an easy to use, hand-held size. The optical sensor can be the test strip itself, or it can be applied to a separate carrier strip.

The optical sensor can be included in a kit, preferably with instructions for use, and materials for taking samples of substances. The optical sensor can also be included as a component of a multi-test device.

A method of making the optical sensor is further detailed below. Briefly, Nafion membrane can be sliced thinly and immersed in a solution including Cu(II) and Nc, and agitated. This impregnates the membrane with the Cu(II)-Nc reagent, resulting in the optical sensor. Preferably, the optical sensor is now the test strip; however, the optical sensor can also subsequently be applied by means known in the art to a separate test strip.

The present invention provides for a method of determining total antioxidant capacity of a substance by applying the optical sensor to a substance, reducing the Cu(II)-Nc reagent with antioxidants in the substance and forming a Cu(I)-Nc chelate, detecting the absorbance or reflectance of the Cu(I)-Nc chelate, and determining the total antioxidant capacity of the substance using the measured absorbance or reflectance. Preferably, the absorbance is detected by inserting the optical sensor in a colorimeter. The sensor and method of the present invention is easily and diversely applicable to conventional laboratories using standard colorimeters rather than necessitating sophisticated equipment and highly qualified operators. An amount of each antioxidant can be detected, and the total antioxidant capacity can be determined by adding the amounts of each individual antioxidant. It is the sum of the antioxidants in the form of total antioxidant capacity that is preferably determined. Uric acid and/or trolox can be used as standards for determining an amount of antioxidants as these components are commonly found in biological fluids such as blood and urine. A standard color change chart that corresponds to mM or μM amounts of the antioxidant can be used to which a sample can be prepared. In other words, the color on the optical sensor after exposure to a sample can be compared to the color on the standard color chart. This can be done visually as well as with a reflective light device or colorimeter. Various other antioxidants can be used as standards such as sulfhydryl groups, vitamin C, flavonoids, etc.

Many different antioxidants can be detected by the above or similar methods of the invention. For example (and by way of illustration and not limitation), the antioxidants can be quercetin, morin, fisetin, myricetin, catechin, kaempferol, rosmarinic acid, gallic acid, naringenin, ascorbic acid, α-tocopherol, uric acid, or bilirubin, as described in TABLE 2. Any other antioxidant can be detected. Combinations of any antioxidants can also be detected. Antioxidants can be detected to assess nutraceuticals.

Furthermore, the total antioxidant capacity of many different substances in trolox or uric acid equivalent units can be determined by the above methods. For example, the substance can be fruits, vegetables, herbal plants, beverages, cereals, any other type of food, biological fluids, or pharmaceuticals. The present invention is very useful to food industry applications for easy, flexible, and low-extracts, special nutritional diets, and functional foods.

The present invention also provides for a method of determining total antioxidant capacity in an individual's physiological fluid by applying the optical sensor to a biological sample from the individual, reducing the Cu(II)-Nc reagent with antioxidants in the biological sample and forming a Cu(I)-Nc chelate, detecting the absorbance of the Cu(I)-Nc chelate, and determining the total antioxidant capacity in the individual's appropriate sample. This method is useful for medicinal food and pharmaceutical industry applications in detection, treatment, and follow-up of special oxidative stress-originated diseases with the advantage of antioxidant measurement in human fluids. For example, antioxidants can be assessed in individuals to assess their risk of developing, or in patients having: cancer, heart disease, metabolic syndrome, type II diabetes, or Alzheimer's disease.

The optical sensor of the present invention can also be used to aid in the assessment of the physiological fitness in an individual by applying the optical sensor to a biological sample from the individual, reducing the CUPRAC reagent (with one example being Cu(II)-Nc reagent) with antioxidants in the biological sample and forming a Cu(I)-Nc chelate, detecting the absorbance of the Cu(I)-Nc chelate, and determining the total antioxidant capacity in the individual. As people age, their natural antioxidant levels are known to decrease. This is also true for sedentary people. Those who exercise regularly can improve their antioxidant activity. This method can be used to assess and monitor the antioxidant activity of individuals in sports medicine and military applications.

As shown below in the Example, the trolox equivalent antioxidant capacity (TEAC) values of various antioxidants using the optical sensor-based cupric reducing antioxidant capacity (CUPRAC) assay were comparable to those of the standard solution-based CUPRAC assay, showing that the membrane-immobilized Cu(II)-Nc reagent retained its reactivity towards antioxidants. The TEAC is defined as the millimolar concentration of a trolox solution having the antioxidant capacity in reducing power equivalent to a 1.0 mM solution of the substance under investigation.

One advantage of the present invention is that the redox reaction giving rise to a colored chelate of Cu(I)-Nc (i.e. CUPRAC chromophore) is relatively insensitive to a number of parameters adversely affecting radicalic reagents such as DPPH, e.g., air, sunlight, humidity, and pH, to a certain extent.

The CUPRAC reagent is fast enough to oxidize thiol-type antioxidants, whereas the FRAP method of the prior art can only measure with serious negative error certain thiol-type antioxidants like glutathione (i.e., the major low molecular weight thiol compound of the living cell). Redox potential of oxidized and reduced forms of glutathione (GSSG/GSH) is the basic indicator of biological conditions of a cell, and GSH acts as a reconstituent of intercellular ascorbic acid from dehydroascorbic acid. Therefore, an antioxidant assay usually responds to GSH.

At least some of the CUPRAC reagent (with examples including Cu(II)-Nc) of present embodiments is selective, because it has a lower redox potential than that of the ferric-ferrous couple in the presence of o-phenanthroline or bathophenanthroline-type ligands (the latter of which can unspecifically oxidize other compounds as well as antioxidants). The standard potential of the Cu(II,I)-Nc redox couple is 0.6 V, close to that of ABTS$^+$/ABTS (E°=0.68 V), and FRAP (E°=0.70 V) reference methods existing in the prior art. Simple sugars, amino acids and citric acid (which are not true antioxidants) are not oxidized with the CUPRAC reagent.

The total antioxidant capacity (TAC) values of antioxidants found with CUPRAC are perfectly additive, i.e., the TAC of a phenolic mixture is equal to the sum of TAC values of its constituent polyphenols. Additivity of TAC values of the mixture constituents in other antioxidant measurements in the prior art is either insufficient or lacking.

Since the product of the redox reaction with antioxidants, a Cu(I)neocuproine complex, retains Cu(I) in the chelated state, redox cycling of antioxidants during antioxidant measurement as observed in FRAP (where Fe(II) is produced, capable of giving rise to Fenton-type undesired oxidation reaction's) is rendered impossible.

Some aspects of invention embodiments are further described in detail by reference to the following experimental examples. These examples are provided for the purpose of illustration only, and are not intended to be limiting. Thus, the invention should in no way be construed as being limited to the following examples, but rather, should be construed to encompass any and all variations which become evident as a result of the teaching provided herein.

Example 1

Instrumentation and Chemicals

The following chemical substances of analytical reagent grade were supplied from the corresponding sources: Neocuproine (2,9-dimethyl-1,10-phenanthroline), morin (MR), quercetin (QR), naringenin (NG), gallic acid (GA), and uric acid (UA): Sigma (Steinheim, Germany); trolox (TR), rosmarinic acid (RA), α-tocopherol (TP) and L-ascorbic acid (AA), Nafion® 115 perfluorinated membrane (thickness 0.005 in.): Aldrich (Steinheim, Germany); copper(II) chloride dihydrate, ammonium acetate ($NH_4Ac$), ethanol (EtOH), and bilirubin (BIL): Merck (Darmstadt, Germany); (+)catechin (CT), myricetin (MYR), fisetin (FS) and kaempferol (K): Fluka (Buchs, Switzerland).

Lipton green tea (camellia sinensis) was purchased from Unilever San. Tic. Turk AS (Istanbul, Turkey), orange and cherry juice from Tamek Gida Konsantre San. Tic. AS (Istanbul, Turkey), apricot and peach juice from Aroma Meyve Sulari Gida San. AS (Bursa, Turkey).

The visible spectra and absorption measurements were recorded in matched quartz cuvettes (using a Varian CARY Bio 100 UV-Vis spectrophotometer (Mulgrave, Victoria, Australia)). The optical thickness of the cuvettes was 1 cm for solution phase, and 1 mm for Nafion solid sensor measurements. Other related apparatus and accessories were Elektromag vortex stirrer (Istanbul, Turkey), BIOSAN Programmable rotator-mixer Bulti Bio RS-24 (Riga, Latvia).

Preparation of Solutions.

$CuCl_2$ solution, $1.0 \times 10^{-2}$ M, was prepared by dissolving 0.4262 g $CuCl_2.2H_2O$ in water, and diluting to 250 mL. Ammonium acetate buffer at pH=7.0, 1.0 M, was prepared by dissolving 19.27 g $NH_4Ac$ in water and diluting to 250 mL. Neocuproine (Nc) solution, $7.5 \times 10^{-3}$ M, was prepared daily by dissolving 0.039 g Nc in absolute ethanol, and diluting to 25 mL with EtOH.

All phenolic compounds were freshly prepared in EtOH at 1 mM concentration and L-ascorbic acid in water at the same concentration. Uric acid (1 mM) and bilirubin (0.5 mM) were prepared in 0.01 M NaOH, and the excess base was neutralized with 0.01 M HCl. The phenolics stock solutions were stored at +4° C. in a refrigerator prior to analysis.

The green tea bag (2 g) was dipped into and pulled out of beakers containing 250 mL freshly boiled water for the first 2 min, and allowed to steep for the remaining 3 min in the covered beakers (total steeping time was 5 minutes). The bag was removed, and the partly turbid solutions were filtered through a black-band Whatman quantitative filter paper after cooling to room temperature.

Example Procedure

I.) Solution-Based CUPRAC Method:

The CUPRAC method is based on the reduction of a cupric neocuproine complex (Cu(II)-Nc) by antioxidants to the cuprous form (Cu(I)-Nc). To a test tube were added 1 mL each of Cu(II), Nc, and $NH_4Ac$ buffer solutions. Antioxidant standard solution (x mL) and $H_2O$ (1.1−x) mL were added to the initial mixture so as to make the final volume: 4.1 mL. The tubes were stoppered, and after ½ hour, the absorbance at 450 nm ($A_{450}$) was recorded against a reagent blank. The scheme for normal measurement of antioxidants is summarized as:

1 mL Cu(II)+1 mL Nc+1 mL buffer+x mL antioxidant soln.+(1.1-x) mL $H_2O$; total volume=4.1 mL, measure ($A_{450}$) against a reagent blank after 30 min of reagent addition.

ii.) Optical Sensor-Based CUPRAC Method:

The commercial Nafion membrane was sliced into 4.5∴0.5 cm pieces, and immersed into a tube containing 2 mL of $2.0 \times 10^{-2}$ M Cu(II)+2 mL of $1.5 \times 10^{-2}$ M Nc+2 mL of 1 M $NH_4Ac$+2.2 mL of $H_2O$, and agitated for 30 minutes in a rotator. The reagent-impregnated membrane was taken out, and immersed in a tube containing 8.2 mL of standard antioxidant or real solutions. The tube was placed in a rotator and agitated for 30 minutes so as to enable color development. The colored membrane was taken out, placed in a 1-mm optical cuvette containing $H_2O$ (to prevent sticking of slices to the walls of the cuvette), and its absorbance at 450 nm was read against a blank membrane prepared under identical conditions excluding analyte.

The calibration curves (absorbance versus concentration graphs) of each antioxidant were constructed under the described conditions, and their trolox equivalent antioxidant capacities (TEAC coefficients, found as the ratio of the molar absorptivity of each compound to that of trolox in the optical sensor-based CUPRAC method) were calculated.

Standard Addition of AA, QR and TP to Green Tea Extract.

A 20-μL aliquot of green tea infusion and 25 μL of 1 mM QR, 200 μL of 1 mM AA or 50 μL 1 mM TP solution were taken into a tube. AA-, QR-, and TP-added solutions were separately subjected to CUPRAC spectrophotometric analysis.

Measurement of Synthetic Mixture Solutions.

Synthetic mixtures of the antioxidants in EtOH were prepared in suitable volume ratios, and these mixtures were diluted to 8.2 mL with EtOH and subjected to optical sensor-based CUPRAC analysis. The theoretical trolox equivalent TAC of a synthetic mixture solution (expressed in the units of mM TR) was calculated by multiplying the TEAC coefficient of each antioxidant constituting the mixture with its final concentration (in mM TR units), and summing up the products. The experimental trolox equivalent TAC of the same mixture was calculated by dividing the observed absorbance ($A_{450}$) to the molar absorptivity of TR ($\epsilon_{TR}$ being $2.40 \times 10^4$ $Lmol^{-1}$ $cm^{-1}$ under the selected conditions). Then the theoretically found TAC were compared to the experimentally observed ones to test the applicability of Beer's law (i.e., the principle of additivity of individual absorbances of constituents making up a mixture). Validity of Beer's law for a mixture implies that the observed absorbance is the sum of the individual absorbances of the constituents.

$$TAC \text{ expected} = TEAC_1 \text{ concn.}_1 + TEAC_2 \text{ concn.}_2 + \ldots + TEAC_n \text{ concn.}_n \quad \text{(Eq. 2.1)}$$

$$TAC \text{ found experimentally} = \frac{\text{Absorbance (total)} \pm \text{intercept}}{\varepsilon_{trolox}} \times 10^3 \quad \text{(Eq. 2.2)}$$

Interference Studies.

The interference effects of 1000-fold (as mole/mole) concomitant species commonly found in fruit juices to the determination of $4.88 \times 10^{-6}$ M QR in ethanolic solution using optical sensor-based CUPRAC methods were studied.

Statistical Analysis.

Descriptive statistical analyses were performed using Excel software (Microsoft Office 2003) for calculating the means and the standard error of the mean. Results were expressed as the mean±standard deviation (SD). Using SPSS software for Windows (version 13), the data were evaluated by two-way ANalysis Of VAriance (ANOVA).

Results and Discussion

Rapid and low-cost chemical sensing of antioxidants with the use of sensors offer significant benefits over the prior art. Optical sensors have the advantages of flexibility and miniaturization, and can also be used for remote sensing. Among optical sensors, colorimetric sensors based either on light absorption at a specified visible wavelength, or the reflection of light from a test matrix have been discovered to offer distinct advantages and benefits within the scope of inventive embodiments.

Moreover, such sensors working in the visible range of the electromagnetic spectrum are not affected from potentially interfering plant pigments essentially absorbing in the UV range, although some utility may also be found when operating in the UV range. Considering the enforced planar (distorted tetrahedral) geometry of cupric chelates when immobilized on membranes, the more beneficial coordination number and geometry of copper compared to iron can enable the design of a more sensitive antioxidant sensor with cupric-neocuproine. A ferric ion-based antioxidant sensor does not exist in the prior art, probably due to the difficulties encountered in fixing the tripositive $Fe(tripyridyltriazine)_2^{3+}$ hydrophilic cation (the FRAP reagent) in a hydrophobic polymer matrix and in regionally achieving a low pH (3.6) on a polymer membrane. Thus, an inexpensive colorimetric sensor was developed, and was effectively used in quantitative TAC assay within the scope of the invention.

Analytical Figures of Merit.

TABLE 1 summarizes the precision and recovery of the optical sensor-based CUPRAC assay using AA, QR, and TP as representative antioxidant compounds. The precision, which is expressed as the relative standard deviation (RSD, %) in absorbance measurement within the tested concentration range, was approximately 6.54%. The recovery of the method varied from 92.8 to 99.9% within individual batches covering vitamins, simple phenolic antioxidants and flavonoids.

Figure 2:
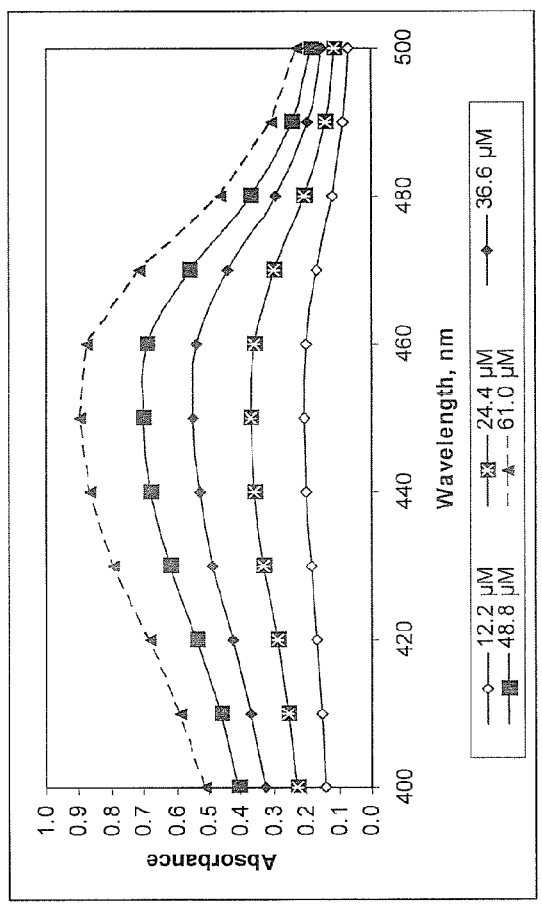
FIG. 2 is a graph of the visible spectra of Cu(I)-Nc chelate produced as a result of optical sensor-based CUPRAC reaction with varying concentrations of trolox.

The recoveries for the individual antioxidant compounds were calculated by means of a CUPRAC calibration curve (as absorbance versus concentration) for the specific antioxidant of concern. FIG. 1 illustrates the redox reaction between one chromogenic oxidizing reagent used for the CUPRAC assay, e.g., bis(neocuproine)copper(II) chloride (Cu(II)-Nc) and antioxidants. This reagent was useful at pH 7, and the absorbance of the Cu(I)-chelate formed as a result of redox reaction with reducing antioxidants (i.e., polyphenolics, vitamins, synthetic antioxidants) was measured at 450 nm. The color was due to the Cu(I)-Nc chelate formed (see FIG. 2, for Cu(I)-Nc spectra obtained by reacting varying concentrations of TR with the CUPRAC reagent).

TABLE 1

Precision and recovery of the optical sensor-based CUPRAC method

| Antioxidant | | Concentration |
|---|---|---|
| Quercetin addition to green tea extract | Added conc. (μM) | 3.05 |
| | Mean (μM) | 2.83 |
| | S.D.[a] | 0.08 |
| | R.S.D., %[b] | 3.16 |
| | REC, %[c] | 92.79 |
| Ascorbic acid addition to green tea extract | Added conc. (μM) | 24.23 |
| | Mean (μM) | 24.20 |

TABLE 1-continued

Precision and recovery of the optical sensor-based CUPRAC method

| Antioxidant | | Concentration |
|---|---|---|
| | S.D.[a] | 0.53 |
| | R.S.D., %[b] | 2.19 |
| | REC, %[c] | 99.87 |
| α-Tocopherol addition to green tea extract | Added conc. (μM) | 6.09 |
| | Mean (μM) | 6.08 |
| | S.D.[a] | 0.39 |
| | R.S.D., X[b] | 6.54 |
| | REC, %[c] | 99.83 |

[a]Standard Deviation.
[b]Relative Standard Deviation.
[c]Recovery (N = 3).

The linear equation for the calibration graph of TR drawn at the wavelength of 450 nm with respect to the optical sensor-based CUPRAC method was:

$$A_{450} = 2.40 \times 10^4 C_{TR} + 0.054 (r=0.999)$$

and the molar absorptivity: $\epsilon = 2.40 \times 10^4$ Lmol$^{-1}$ cm$^{-1}$. The limit of detection (LOD) and limit of quantification (LOQ) for TR in the optical sensor-based CUPRAC assay were calculated using the equation; LOD=3 $S_{bi}$/m and LOQ=10 $S_{bi}$/m, respectively, where $S_{bi}$ is the standard deviation of a blank and m is the slope of the calibration line. The LOD and LOQ for TR were found to be 1.01 and 3.33 μM, respectively. The precision, which is expressed as the relative standard deviation (RSD, %) in the tested concentration range, was approximately 5.20%. CUPRAC absorbances of TR were linear within the concentration range of $4.11 \times 10^{-8}$–$5.18 \times 10^{-5}$ M (as final concentrations in solution), and the method showed excellent linearity (r=0.999) over a relatively broad concentration range of analyte, a condition not frequently experienced in solid sensors.

To determine the reproducibility of the method, a ruggedness experiment was performed. The optical sensor-based CUPRAC procedure for fruit samples gave intra- and inter-assay coefficient of variation (CV)s around 1.03% and 5.71%.

The cupric-neocuproine loaded (single-use) sensor was tested for stability, and was shown to lose only 3% signal intensity after 15 days-storage in distilled water kept in a dessicator at room temperature.

The correlation between the CUPRAC absorbance (A) for a given antioxidant compound (ascorbic acid, α-tocopherol, trolox, uric acid, bilirubin, and other phenolic antioxidants) and its molar concentration (c) was evaluated using fourteen compounds. TABLE 2 summarizes the linear equations (A=mC+n), correlation coefficients (r), and linear concentration ranges of these pure compounds. As can be seen from TABLE 2, all antioxidants could be assayed with the optical sensor-based CUPRAC assay (TEAC coefficients (significantly different) and (P=0.05, $F_{exp}$=0.681, $F_{crit}$(table)=4.667, $F_{exp} < F_{crit}$ (table))). The TEAC coefficients found by the optical sensor-based CUPRAC method correlated well (r=0.876) with those of the solution-based CUPRAC method (TABLE 2). If serum antioxidants are excluded, the correlation coefficient for twelve compounds is raised to r=0.957. Charge transport in solid polymer matrixes with redox centers in their ground state can involve various mechanisms such as physical diffusion of redox species, and these mechanisms can be quite different from those in aqueous solution. The redox reactions of antioxidants with the Nafion membrane-fixed reagent, cupric neocuproine, initially requires the physical diffusion of the antioxidant to the membrane surface, decreasing the reaction rate with respect to that in bulk solution. The steric hindrance caused by the bulky substituents of the polyphenol and the immobilized oxidizing reagent is also a slowing factor for electron transfer, whereas the local enrichment of the oxidizing reagent for antioxidant molecules diffused to the membrane surface is a rate enhancing factor compared to that in solution. These conflicting factors show that there may not be an exact one-to-one correspondence between the TEAC values of antioxidants measured with the solution- and sensor-based CUPRAC procedures (TABLE 2). The large TEAC value of bilirubin can possibly be attributed to the 450-nm absorption interference of biliverdin emerging as the oxidation product of bilirubin. Nevertheless, the slope of the calibration line is still close to unity (i.e., $TEAC_{solution} = 1.033$ $TEAC_{sensor} + 0.099$).

All of the easily oxidized flavonoids exhibited standard reduction potentials of ≤0.2 V, whereas naringenin, having a potential close to that of the Cu(Nc)$_2^{2+}$—Cu(Nc)$_2^+$ couple, underwent a slow reaction with the reagent. Naringenin oxidation was only forced to completion after 50° C. incubation in the solution-based CUPRAC method (TEAC coefficient for NG=0.05). In the optical sensor-based CUPRAC method, NG was directly assayed without incubation, the corresponding TEAC coefficient being 0.60. The TEAC-CUPRAC coefficients of NG in pure EtOH and MeOH were 0.05 and 0.57, respectively, probably due to facilitated e-transfer in ionizing solvents capable of anion (phenolate) solvation, because MeOH is the alcohol that best supports ionization. Compared to aqueous medium, the sensor membrane can also be considered to be a less hydrophilic medium like MeOH, enhancing e-transfer. Moreover, by embedding a cationic redox-active metal complex (Cu(Nc)$_2^{2+}$) into a water-insoluble anionic polymer such as Nafion, a molecular aggregate can be formed showing a unique and active redox behavior that cannot be achieved with either a homogeneous solution or a neat catalyst. Such a confinement of the redox-active complex can increase its local concentration (compared to that in homogeneous solution), thereby increasing the redox reaction rate (e.g., for naringenin).

As opposed to the enhanced antioxidant power of naringenin, catechin and rosmarinic acid exhibited significantly lower TEAC coefficients on the sensor membrane (than in solution) (TABLE 2). Catechin lacks the 2,3-double bond conjugated with the 4-oxo group responsible for electron delocalization, which is considered to be an important prerequisite for high antioxidant power. The superior antioxidant ability of quercetin results from the formation of a stable aryloxy radical, due to C2-C3 double bond and the resulting planar geometry which delocalizes the radical throughout the entire molecule, whereas A and B rings are perpendicular to each other in catechin. When the aryloxy radical produced from 1-e oxidation of a flavonoid is stabilized by conjugation, the redox potential of the flavonoid is lowered, increasing its antioxidant power. Considering the enforced planar geometry of copper-neocuproine on the sensor membrane, lack of planarity of catechin is an important drawback playing part in the decreased antioxidant power of CT. On the other hand, in spite of the four phenolic —OH groups and excellent conjugated structure of rosmarinic acid, its TEAC coefficient in the sensor assay decreased, probably due to its large molecular size being an important parameter in optical sensor response, and its low p$K_a$ which is 2.8. Likewise, the relatively decreased TEAC capacity of ascorbic acid (with respect to that measured in the solution phase CUPRAC method) can be attributed to its negative charge at pH=7, since ascorbic acid is in the form of monohydrogen ascorbate (p$K_{a1}$=4.2 and p$K_{a2}$=11.6) at the working pH of the sensor, and should essentially be repelled by the negatively charged Nafion membrane.

TABLE 2

The linear calibration equations, TEAC coefficients, and linear concentration range of the tested antioxidants with respect to the optical sensor-based CUPRAC method.

| Antioxidants | Linear equation and correlation coefficient | Linear range (M) | TEAC (optical sensor-based CUPRAC) | TEAC (solution-based CUPRAC) |
|---|---|---|---|---|
| Quercetin (QR) | $A = 9.88 \times 10^4 c + 0.015$<br>$r = 0.998$ | $3.52 \times 10^{-7}$-$1.30 \times 10^{-5}$ | 4.11 | 4.38 |
| Morin (MR) | $A = 4.61 \times 10^4 c + 0.018$<br>$r = 0.996$ | $6.95 \times 10^{-7}$-$2.77 \times 10^{-5}$ | 1.92 | 1.88 |
| Fisetin (FS) | $A = 7.44 \times 10^4 c + 0.016$<br>$r = 0.999$ | $6.20 \times 10^{-8}$-$2.05 \times 10^{-5}$ | 3.10 | 3.90 |
| Myricetin (MYR) | $A = 3.31 \times 10^4 c - 0.034$<br>$r = 0.999$ | $2.53 \times 10^{-6}$-$4.02 \times 10^{-5}$ | 1.38 | 1.38 |
| Catechin (CT) | $A = 4.61 \times 10^4 c + 0.054$<br>$r = 0.999$ | $1.30 \times 10^{-7}$-$2.70 \times 10^{-5}$ | 1.92 | 3.09 |
| Kaempferol (K) | $A = 2.95 \times 10^4 c + 0.106$<br>$r = 0.996$ | $1.35 \times 10^{-7}$-$4.04 \times 10^{-5}$ | 1.23 | 1.58 |
| Rosmarinic acid (RA) | $A = 9.19 \times 10^4 c - 0.015$<br>$r = 0.999$ | $7.14 \times 10^{-7}$-$1.43 \times 10^{-5}$ | 3.83 | 5.30 |
| Gallic acid (GA) | $A = 5.06 \times 10^4 c + 0.002$<br>$r = 0.999$ | $9.44 \times 10^{-7}$-$2.56 \times 10^{-5}$ | 2.10 | 2.62 |
| Naringenin (NG) | $A = 1.46 \times 10^4 c + 0.005$<br>$r = 0.999$ | $3.05 \times 10^{-6}$-$8.86 \times 10^{-5}$ | 0.60 | 0.05 |
| Ascorbic acid (AA) | $A = 1.71 \times 10^4 c - 0.059$<br>$r = 0.999$ | $6.36 \times 10^{-6}$-$7.93 \times 10^{-5}$ | 0.71 | 0.96 |
| α-Tocopherol (TP) | $A = 3.11 \times 10^4 c - 0.010$<br>$r = 0.999$ | $1.94 \times 10^{-6}$-$4.21 \times 10^{-5}$ | 1.29 | 1.10 |
| Uric acid (UA) | $A = 3.30 \times 10^4 c + 0.129$<br>$r = 0.999$ | $1.51 \times 10^{-7}$-$3.54 \times 10^{-5}$ | 1.38 | 0.96 |
| Bilirubin (BIL) | $A = 1.10 \times 10^5 c + 0.076$<br>$r = 0.995$ | $2.20 \times 10^{-8}$-$1.11 \times 10^{-5}$ | 4.58 | 3.18 |

TEAC coefficients (significantly different);
($P = 0.05$, $F_{exp} = 0.681$, $F_{crit\ (table)} = 4.667$, $F_{exp} < F_{crit\ (table)}$).
$TEAC_{solution} = 1.033\ TEAC_{sensor} + 0.099$ ($r = 0.876$)

TAC Measurement of Synthetic Mixture Solutions.

Synthetic mixtures of antioxidants exhibited the theoretically expected antioxidant capacities (TAC) within ±6.8% (TABLE 3), meaning that chemical deviations from Beer's law were essentially absent, and the CUPRAC absorbances of constituents of antioxidant mixtures were additive. The original CUPRAC method was previously shown to be free from chemical deviations from Beer's law, as demonstrated on synthetic mixtures of hydrophilic phenolic compounds. This is a prerequisite for precise estimation of antioxidant capacity, as the capacity of a mixture should be composed of the sum of individual capacities of constituents in order to make reliable comparisons of the antioxidant power of different foodstuffs.

The two-way Analysis Of Variance (ANOVA) comparison by the aid of F-test of the mean-squares of "between-treatments" (i.e., theoretically expected capacity with respect to optical sensor-based CUPRAC method and experimentally found capacities of different mixtures in TABLE 3) and of residuals for a number of real samples (consisting of synthetic mixtures of antioxidants) enabled to conclude that there was no significant difference between the population means for a given sample. In other words, the experimentally found capacity results and theoretically expected capacity calculations were alike at 95% confidence level ($F_{exp}$=0.001, $F_{crit}$=10.13, $F_{exp}<F_{crit}$ at P=0.05). Thus, the proposed methodology was validated for synthetic mixtures of antioxidants of differing lipophilicity. On the other hand, there was significant difference between samples with respect to composition of mixtures (i.e., the 'residual' mean-square was much greater than 'between-sample' mean-square at 95% confidence level). This was natural, as these mixtures were deliberately prepared at different total concentrations of trolox equivalents.

TABLE 3

Comparison of the theoretically expected and experimentally found trolox (TR)- equivalent antioxidant capacities (in mM TR units) of synthetic mixtures of antioxidants (with respect to the optical sensor-based CUPRAC assay).

| Number | Composition of mixture | Capacity expected (as mM TR-equivalent) | Capacity found experimentally (as mM TR-equivalent) |
|---|---|---|---|
| 1 | 25 µL 1 mM QR<br>50 µL 1 mM GA<br>50 µL 1 mM KM | $4.25 \times 10^{-2}$ | $(4.07 \pm 0.30) \times 10^{-2}$ |
| 2 | 60 µL 1 mM MOR<br>50 µL 1 mM TR<br>25 µL 1 mM RA | $3.18 \times 10^{-2}$ | $(3.22 \pm 0.19) \times 10^{-2}$ |
| 3 | 25 µL 1 mM QR<br>60 µL 1 mM MOR<br>25 µL 1 mM RA | $3.82 \times 10^{-2}$ | $(4.08 \pm 0.13) \times 10^{-2}$ |
| 4 | 50 µL 1 mM GA<br>50 µL 1 mM TR<br>50 µL 1 mM KM | $3.61 \times 10^{-2}$ | $(3.50 \pm 0.13) \times 10^{-2}$ |

Samples were analyzed in triplicate.
|(P = 0.05, $F_{exp} = 0.001$, $F_{crit\ (table)} = 10.13$, $F_{exp} < F_{crit\ (table)}$).

TAC Measurement of Fruit Juices.

Figure 3:
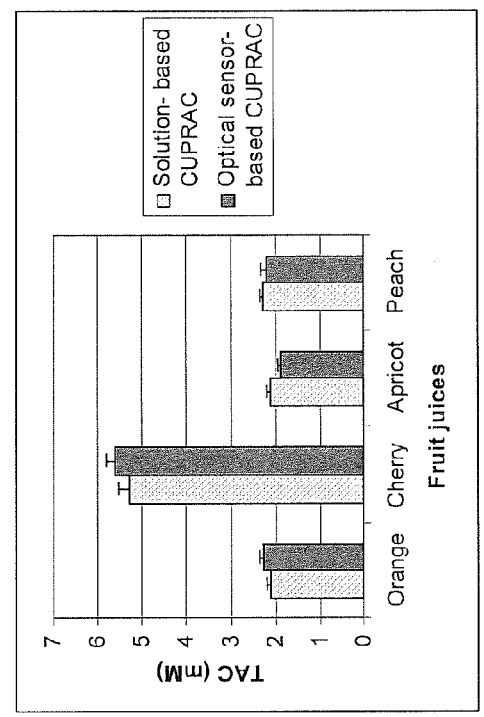
FIG. 3 is a graph of TAC values (in mM Trolox equivalent units) of some commercial fruit juices using the solution-based and optical sensor-based CUPRAC assays.

In FIG. 3, the optical sensor-based and solution-based $TAC_{CUPRAC}$ values of fruit juices were reported as trolox equivalents (mM TR). The hierarchy for TAC of fruit juices with respect to optical sensor-based CUPRAC method was: apricot<peach<orange<cherry. Linear regression analysis of capacity data presented in FIG. 3 found with the solution-based CUPRAC assay showed that this assay correlated well with the optical sensor-based CUPRAC assay.

Interferences in the optical sensor-based CUPRAC assay. For the developed sensing method, the possible interference effects of 1000-fold (as mole/mole) concomitant species commonly found in fruit juices on the determination of $4.88 \times 10^{-6}$ M QR in ethanolic solution are shown in TABLE 4. The presence of 1000-fold citrate, oxalate and tartarate ions that can be found in fruit juices and other food plant extracts did not interfere with the CUPRAC reaction forming the basis of sensor measurement.

TABLE 4

Interference of various molecular species with the optical sensor-based CUPRAC assay of $4.88 \times 10^{-6}$ M quercetin (OR) in ethanolic solution.

| Interferent | Interferent/QR mole ratio | Presence (+) or absence (−) of interference with the optical sensor-based CUPRAC method |
|---|---|---|
| Oxalate | 1000 | − |
| Tartarate | 1000 | − |
| Citrate | 1000 | − |
| Glucose | 1000 | − |
| Malic acid | 1000 | − |
| Fumaric acid | 1000 | − |
| Fructose | 1000 | − |
| Galactose | 1000 | − |
| Nitrite | <50 | + |

The QR and interferent concentrations in final solution were $4.88 \times 10^{-6}$ and $4.88 \times 10^{-3}$ M, respectively.

CONCLUSIONS

Through invention embodiments, the Cu(II)-Nc reagent was electrostatically immobilized onto a cation exchanger Nafion membrane, and was demonstrated to retain its reactivity towards various antioxidants after incorporation into the exchanger membrane. The developed optical sensor was validated to quantify antioxidants over a wide concentration range in comparison to solution-phase methods, and showed good sensitivity for antioxidant detection in complex samples such as fruit juices. The optical sensor-based CUPRAC assay can be used for quantitative assessment of total antioxidant capacity of complex mixtures in trolox equivalent units. Common food ingredients like oxalate, citrate, fruit acids and common sugars did not interfere with the proposed sensing method. This and other methods and systems of the invention offer advantages over prior art solution-based assays, including the ability of being used as a rapid, low-cost, diversely and easily applicable screening tool for TAC of plant and food extracts of unknown composition without pretreatment, and of being in a kit format.

Throughout this application, various publications, including United States patents, are referenced by author and year and patents by number. Full citations for the publications are listed below. The disclosures of these publications and patents in their entireties are hereby incorporated by reference into this application as necessary in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that the invention can be practiced otherwise than as specifically described.

The invention claimed is:

1. An apparatus for measuring antioxidant capacity in a biological sample comprising:
   a solid media, wherein the solid media is composed of paper or woven fabrics; and,
   a reagent carried by the media, wherein the reagent is comprised of copper and neocuproine (2,9-dimethyl-1,10-phenanthroline, abbreviated as Nc) chelator embedded in or adsorbed to the solid media and wherein the reagent is reactive with a number of antioxidants in a biological sample to cause changes in light that are incident upon the reagent while carried by the solid media, wherein the reagent has a standard reduction potential of about 0.6V.

2. An apparatus as defined by claim 1 wherein the changes in light comprise one or more of changes in the spectral absorbance of the reagent and changes in the reflectance of the reagent retained on a solid medium.

3. An apparatus as defined by claim 1 wherein the reagent is electrostatically immobilized on the media.

4. An apparatus as defined by claim 1 wherein the changes in light are generally linear with antioxidant concentration.

5. An apparatus as defined by claim 1 wherein the changes in light are additive for different antioxidants wherein the change indicates concentration of all antioxidants.

6. An apparatus as defined by claim 1 wherein:
   the reagent comprises a Cu(II)-Nc reagent; and,
   reaction of the reagent with the antioxidant comprises reduction of the Cu(II)-Nc reagent to form a Cu(I)-Nc chelate in or on the solid phase matrix.

7. An apparatus as defined by claim 1 and further comprising:
   a light source for illuminating the media following reaction with the reagent; and,
   an optical sensor for determining a measurement of light that is one or more of reflected from the media or transmitted through the media.

8. An apparatus as defined by claim 7 and further comprising a reference for comparing the optical sensor light measurement to, the comparison useful to determine total antioxidant capacity.

9. A solid phase antioxidant assay apparatus comprising:
   a solid phase matrix, wherein the solid phase matrix is solid media composed of paper or woven fabrics;
   an impregnated in the solid media copper(II)-neocuproine reagent that oxidizes one or more antioxidants as they contact the reagent, the copper(II)-neocuproine reagent undergoing a change through the copper(II)-neocuproine reduction that causes changes in light reflected from the immobilized reagent, with the changes being proportional with antioxidant concentration over a certain antioxidant concentration range, wherein the reagent has a standard reduction potential of about 0.6V;
   a light source for illuminating the impregnated solid media;
   a light sensor for determining a measurement of light reflected from the impregnated solid media; and,
   a reference for comparing the measurement to, the comparison useful to indicate concentration of the antioxidant.

* * * * *